(12) United States Patent
Taylor et al.

(10) Patent No.: US 9,079,017 B2
(45) Date of Patent: Jul. 14, 2015

(54) FRACTAL INTERCONNECTS FOR NEURO-ELECTRONIC INTERFACES AND IMPLANTS USING SAME

(75) Inventors: Richard P. Taylor, Eugene, OR (US); Simon A. Brown, Christchurch (NZ)

(73) Assignees: University of Oregon, Eugene, OR (US); University of Canterbury, Christchurch (NZ)

( * ) Notice: Subject to any disclaimer, the term of this patent is extended or adjusted under 35 U.S.C. 154(b) by 1037 days.

(21) Appl. No.: 12/931,978

(22) Filed: Feb. 15, 2011

(65) Prior Publication Data

US 2012/0209350 A1   Aug. 16, 2012

(51) Int. Cl.
*A61N 1/04* (2006.01)
*A61N 1/05* (2006.01)
*B82Y 30/00* (2011.01)
*A61N 1/36* (2006.01)

(52) U.S. Cl.
CPC ............ *A61N 1/0543* (2013.01); *A61N 1/0526* (2013.01); *B82Y 30/00* (2013.01); *A61N 1/36103* (2013.01)

(58) Field of Classification Search
CPC ............ A61N 1/36103; A61N 1/0526; A61N 1/05243
USPC .......................................... 607/116, 117, 118
See application file for complete search history.

(56) References Cited

U.S. PATENT DOCUMENTS

| | | | |
|---|---|---|---|
| 4,903,702 A * | 2/1990 | Putz | 600/377 |
| 6,292,703 B1 | 9/2001 | Meier et al. | |
| 6,427,087 B1 | 7/2002 | Chow et al. | |
| 6,522,924 B1 | 2/2003 | Meier | |
| 6,727,863 B2 | 4/2004 | Wen et al. | |
| 6,974,533 B2 | 12/2005 | Zhou | |
| 7,259,324 B2 | 8/2007 | Zeira | |
| 7,272,447 B2 | 9/2007 | Stett et al. | |
| 7,338,522 B2 | 3/2008 | Greenberg et al. | |
| 7,494,907 B2 | 2/2009 | Brown et al. | |
| 7,666,523 B2 | 2/2010 | Zhou | |
| 2007/0198066 A1 | 8/2007 | Greenberg et al. | |
| 2008/0071340 A1 | 3/2008 | Atanasoska et al. | |

OTHER PUBLICATIONS

Humayun, et al., "Towards a completely implantable, light-sensitive intraocular retinal prosthesis" Proceedings of the 23rd Annual International Conference of the IEEE Engineering in Medicine and Biology Society, 2001, vol. 4, pp. 3422-3425.

(Continued)

*Primary Examiner* — Alyssa M Alter
(74) *Attorney, Agent, or Firm* — Lumen Patent Firm

(57) ABSTRACT

A neuro-electronic interface device has a micro-electrode electrically connected to an interconnect that has scaling gradients between 1.1 and 1.9 over a scaling range of at least one order of magnitude. The device preferably has an array of such fractal interconnects in electrical contact with an array of micro-electrodes. Such fractal interconnect arrays may be components of implants including a retinal implant device having an array of photodetectors in electrical contact with the array of micro-electrodes. The interconnects may be fabricated by forming nanoscale particles and depositing them onto a non-conductive surface that is smooth except for electrodes which serve as nucleation sites for the formation of fractal interconnect structures through diffusion limited aggregation.

7 Claims, 12 Drawing Sheets

(56) References Cited

OTHER PUBLICATIONS

Subasinghe, "Applications of Non-Linear Dynamics in the Production of Functionalised and Sensing Material," Advanced Materials Research (vols. 93-94), Jan. 2010, pp. 485-488.

Wen et al., "Infrared passbands from fractal slit patterns on a metal plate," Appl.Phys.Lett., vol. 83, No. 11 (2003), p. 2106-2108.

Bardotti et al., "Organizing nanoclusters on functionalized surfaces," Appl. Surf. Sci., vol. 191 (2002), pp. 205-210.

Bréchignac et al., "Coulombic fission and evaporation of antimony cluster ions," J. Chem. Phys., vol. 102, No. 2, Jan. 8, 1995, pp. 763-769.

Scott et al., "Three-dimensional growth characteristics of antimony aggregates on graphite," Eur. Phys. J. D, vol. 39, pp. 433-438 (2006).

Witten et al., "Diffusion-limited aggregation," Phys. Rev. B, vol. 27, No. 9, May 1, 1983.

Carlier et al., "Dynamics of Polymorphic Nanostructures: From Growth to Collapse," Nano Letters, vol. 6, No. 9, (2006), pp. 1875-1879.

Zrenner et al., "Subretinal electronic chips allow blind patients to read letters and combine them to words," Proc. R. Soc. B, Nov. 3, 2010, vol. 278, pp. 1489-1497.

Veraart et al., "Visual sensations produced by optic nerve stimulation using an implanted self-sizing spiral cuff electrode," Brain Research, vol. 813 (1998), pp. 181-186.

Yoon et al., "Morphology control of the supported islands grown from soft-landed clusters," Surface Science, vol. 443 (1999), pp. 76-88.

Kolb, "How the Retina Works," American Scientist, vol. 91 (2003), p. 28-35.

H. Brune. "Microscopic view of epitaxial metal growth: nucleation and aggregation." Surface Science Reports, 31, 121-229, (1998).

A. Y. Chow et al., "Subretinal electrical stimulation of the rabbit retina," Neurosci. Lett. 225, 13-16 (1997).

A. Y. Chow et al., "The Artificial Silicon Retina Microchip for the Treatment of Vision Loss From Retinitis Pigmentosa," Arch Ophthalmol. 122, 460-469 (2004).

W. de Heer, "The physics of simple metal clusters: experimental aspects and simple models," Rev. Mod. Phys. 65, 611 (1993).

J. E. Ferguson et al "Creating low Impedance tetrodes by electroplating with additives", Sensors and Actuators A, 156 388-393 (2009).

E. Guenther et al., "Long-term survival of retinal cell cultures on retinal implant materials," Vision Res. 39: 3988-3994 (1999).

T.A. Kuiken et al, "Redirection of cutaneous sensation from the hand to the chest skin of human amputees with targeted reinnervation", PNAS, 104, 20061, (2007).

D. N. McCarthy. "Nucleation and Equilibration via Surface Diffusion: An Experimental Study." PhD thesis, University of Canterbury, Christchurch, New Zealand, 2008.

S. J. Tans et al., "Room-temperature transistor based on a single carbon nanotube," Nature, vol. 393, pp. 49-52 (May 7, 1998).

B. von Issendorff et al., "A new high transmission infinite range mass selector for cluster and nanoparticle beams," Rev. Sci. Instr., vol. 70, No. 12 (1999), pp. 4497-4501.

Z. Zhang et al., "Bonding-geometry dependence of fractal growth on metal surfaces." Phys. Rev. Lett., 73, 1829-32, (1994).

* cited by examiner

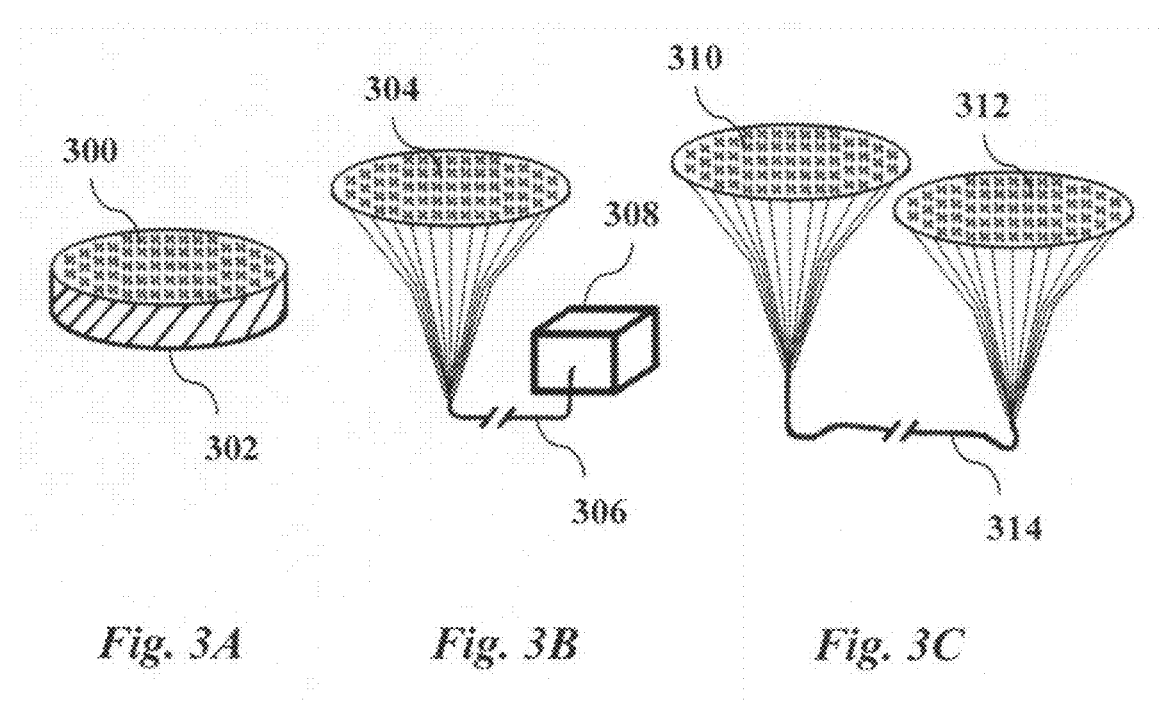
*Fig. 3A*     *Fig. 3B*     *Fig. 3C*

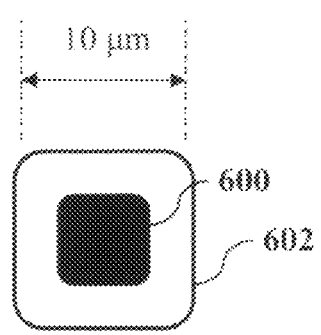
*Fig. 6A*
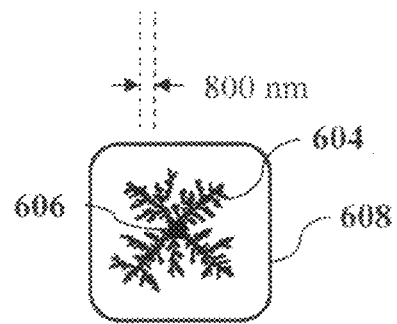
*Fig. 6B*
*Fig. 7A*
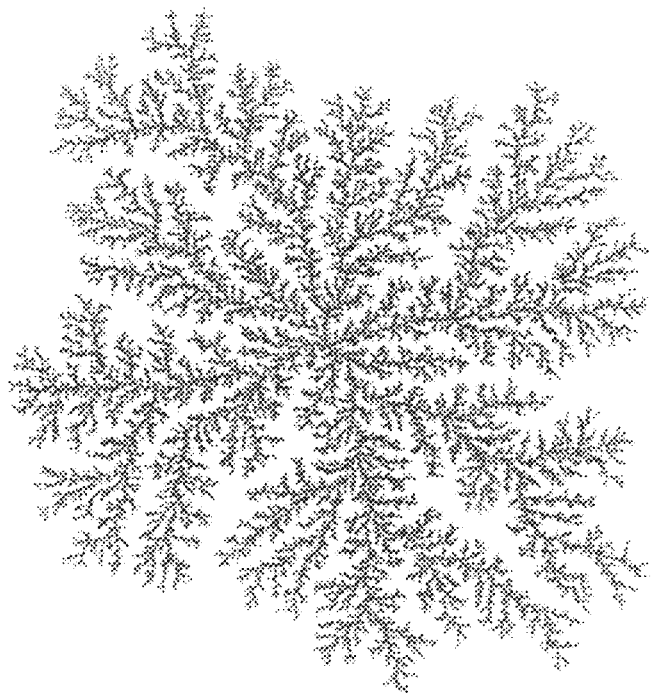
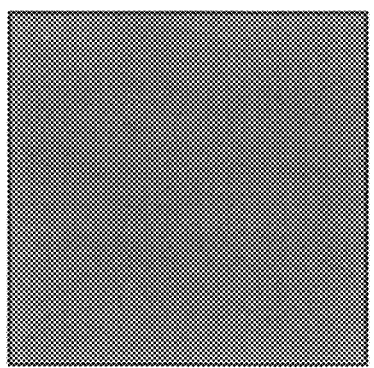
*Fig. 7C*
*Fig. 7B*

Fig. 9A
Fig. 9B
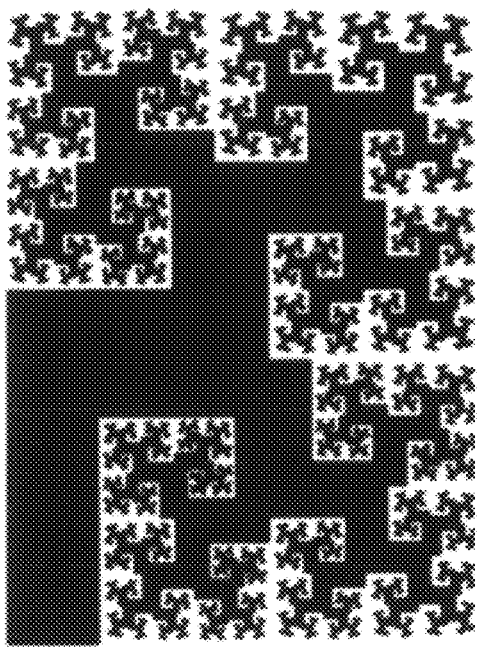
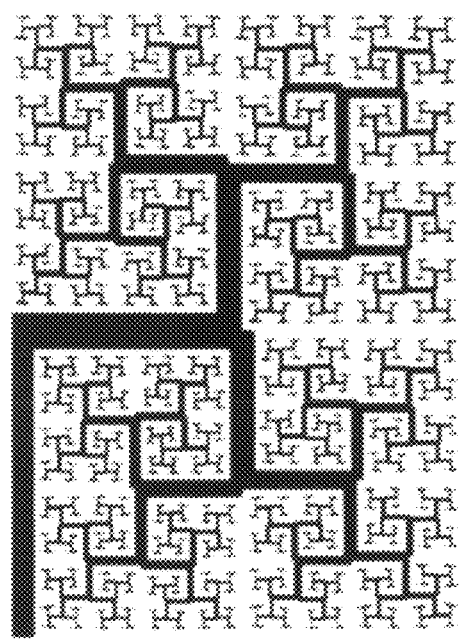

FRACTAL INTERCONNECTS FOR NEURO-ELECTRONIC INTERFACES AND IMPLANTS USING SAME

STATEMENT OF GOVERNMENT SPONSORED SUPPORT

This invention was made with Government support under contract FA8650-05-5-5041 awarded by the Air Force Research Lab, and under contract N00014-10-1-0082 awarded by the Office of Naval Research. The Government has certain rights in this invention.

FIELD OF THE INVENTION

The present invention relates generally to artificial electronic implants for humans and animals. More specifically, it relates to techniques and devices for neuro-electronic interface devices used to form a connection between an electronic implant and biological neurons.

BACKGROUND OF THE INVENTION

Electronic implants can dramatically improve the quality of human life. Due to the development of nanoelectronics, there is now the possibility of integrating implants with more sophisticated physiological systems such as the visual system.

The visual system includes the retina, which receives light and converts it into electrical signals; the optic nerve, which communicates the signals from the retina to the brain; and the visual regions of the brain, which process the signals. Diseases such as macular degeneration deteriorate the retina while leaving the optic nerve healthy. Accordingly, to restore vision, researchers have proposed artificial retinal implants made using semiconductor chips that interface with healthy retinal neurons and communicate visual signals to the optic nerve. Retinal implants are promising because these semiconductor chips have not been rejected by the surrounding organic tissue of the eye and also because the brain and optical neurons have the capacity to learn how to interpret the signals originating from the retinal implants.

As shown in FIG. 1A, the retina has a layer of photoreceptors (rods and cones) 100 which detect incoming light 108. The layer of photoreceptors 100 is positioned behind a natural electrical circuit called the plexiform layer 102 which provides local processing of the electrical signal before passing the signal to the optic nerve (not shown). There are two general classes of retinal implants: epiretinal implants (FIG. 1B) and subretinal implants (FIG. 1C). As shown in FIG. 1B, an epiretinal implant 106 sits in front of the plexiform layer 102. In one epiretinal implant design, the implanted chip 106 wirelessly receives visual signals detected by a camera external to the eye. In contrast to the epiretinal implant, a subretinal implant 104, as shown in FIG. 1C, sits behind the plexiform layer 102, taking the place of deteriorated photoreceptors. One type of subretinal implant includes an array of photodiodes that convert light into electrical signals. For example, FIG. 2A is a close-up view showing a small portion of an array of 5000 photodiodes of a conventional subretinal implant. Each photodiode 200 in the array has a corresponding electrode 202 positioned at its center. When light is detected by photodiode 200, an electrical signal is communicated through the electrode 202 to the retinal neurons in the plexiform layer. FIG. 2B illustrates a retinal neuron having a central body called the soma 204 and branched projections called dendrites. The soma 204 is approximately 10 μm in width and the dendrites can extend the width of the neuron up to 100 μm. When dendrites connect with the electrode 202 of the implant, they form a neuro-electronic interface allowing the signals from the photodiode 200 to be communicated to the neuron and through the plexiform layer to the optical nerve and brain. The electrode 202 thus serves as a neuro-electronic interconnect of the implant.

The neuro-electronic interface between the electrode 202 and neuron is critical to the performance of the retinal implant. The design shown in FIG. 2A, however, has several potential problems. One significant problem is that electrical signals from the electrodes may damage the plexiform layer due to a capacitance overload at the interface or induce toxins due to polarization of electrolytic bio-fluid at the interface. One proposal for improving a neuro-electronic interface is to increase the roughness of the surface of the electrode. The increased surface area of the electrode is thought to reduce the probability that electrical signals will damage the neuro-electronic interface. This approach, however, does not solve other problems with the design.

Another potential problem is that many electrodes in the array may be unconnected or poorly connected to neurons in the plexiform layer. Although photodiodes can be fabricated with packing densities approaching those of the rods and cones in the human retina, a person with an artificial retina might still only be able to see a small fraction of the detail generated by the implant. Although increasing the size of each electrode 202 might be expected to improve the likelihood that it will connect with a neuron, this approach is not feasible for a retinal implant since it would obscure light from reaching the underlying photodiode 200 and defeat the fundamental purpose of the implant. The current design of FIG. 2A, in other words, suffers from a trade-off between capacity to sense light and capacity to communicate the resulting electrical signals to the neurons of the plexiform layer. There is thus a need for an improved method for forming a neuro-electronic interface which addresses the above limitations.

Moreover, electronic implants in other parts of the body also suffer from similar challenges related to insufficient number of neuro-electrical connections. Prosthetic hands, for example, do not have an adequate connection with the nerves to provide an adequate sense of touch. Similarly, the number of connections between neurons and electrodes implanted into mammalian brains is insufficiently large to accurately target neurons requiring electrical stimulation. The same problem is faced by implants designed to interface two parts of a biological system that have lost their natural connection. In each case, the functionality of the implant is limited by the performance of the neuro-electrical interface between the artificial and biological systems.

Accordingly, it is an object of the invention to address one or more of the above-mentioned disadvantages with current neuro-electronic interface techniques.

SUMMARY OF THE INVENTION

In one aspect, a neuro-electronic interface device is provided having a micro-electrode and an interconnect in electrical contact with the micro-electrode, where the interconnect is conductive, is fabricated on a non-conductive surface, and has scaling gradients that can range between 1.1 and 1.9 over a scaling range of at least one order of magnitude. In some cases, the interconnect has a fractal dimension D between 1.4 and 1.9 over a scaling range of at least one order of magnitude below 200 μm. In some cases, the interconnect has a fractal dimension between 1.6 and 1.9 over a scaling range of at least two orders of magnitude below 200 μm. In various embodiments, the device has an array of micro-electrodes and an array of interconnects in electrical contact with the array of micro-electrodes, where the interconnects are in one-to-one correspondence with the micro-electrodes. In some embodiments, the device has an electrode fabricated on an atomically smooth substrate. In some embodiments, the device has a non-conductive planar layer fabricated on a substrate, where the micro-electrode is fabricated on the substrate, the interconnect is fabricated on the planar layer, and a surface roughness of the planar layer is less than a surface roughness of the substrate. In some cases the planar layer has a mean roughness (Rms) less than 1 nm. In some cases the planar layer is atomically smooth. In some embodiments, the interconnect consists of an assembly of nanoscale particles.

In another aspect, a retinal implant device is provided having an array of photodetectors, an array of micro-electrodes in electrical contact with the array of photodetectors, and an array of neuro-electronic interconnects in electrical contact with the array of micro-electrodes, where the neuro-electronic interconnects are in one-to-one correspondence with the micro-electrodes, and where each of the neuro-electronic interconnects has scaling gradients that can range between 1.1 and 1.9 over a scaling range of at least one order of magnitude. In some cases, the interconnect has a fractal dimension D between 1.4 and 1.9 over a scaling range of at least one order of magnitude below 200 μm. In some cases the interconnect has a fractal dimension between 1.6 and 1.9 over a scaling range of at least two orders of magnitude below 200 μm.

In another aspect, a method is provided for fabricating a neuro-electronic interconnect. The method includes providing a micro-electrode array comprising a collection of electrodes and a non-conductive planar layer forming an interspace between the electrodes, forming nanoscale particles, and depositing the nanoscale particles onto the planar layer to produce conductive interconnects in electrical contact with the electrodes. The depositing of the nanoscale particles includes controlling a diffusivity of the clusters such that each of the produced interconnects has scaling gradients that can range between 1.1 and 1.9 over a scaling range of at least one order of magnitude. In some cases, the interconnect has a fractal dimension D between 1.4 and 1.9 over a scaling range of at least one order of magnitude below 200 μm. In some cases, the diffusivity is controlled such that each of the produced interconnects has a fractal dimension D between 1.6 and 1.9 over a scaling range of at least two orders of magnitude below 200 μm. Implementations of the method may include forming the nanoscale particles by a) inert gas aggregation, b) atomic cluster evaporation (from a crucible). In some embodiments of the method, the micro-electrode array comprises a substrate, the electrodes are fabricated on the substrate, and the method includes depositing the planar layer onto the substrate of the micro-electrode array such that the planar layer covers the planar substrate but does not completely cover the electrodes, and a surface roughness of the planar layer is less than a surface roughness of the substrate. In some cases depositing the planar layer is performed such that the deposited planar layer has a mean roughness (Rms) less than 1 nm.

BRIEF DESCRIPTION OF THE DRAWINGS

FIG. 3A is a schematic diagram of an implant that connects to neuronal circuitry via an array of fractal interconnects, according to an embodiment of the invention.

FIG. 3B is a schematic diagram of an device with an array of fractal interconnects and an external device for measuring electrical signals or stimulating neuronal activity, according to an embodiment of the invention.

FIG. 3C is a schematic example of an implant in which two arrays of fractal interconnects are connected via wires, according to an embodiment of the invention.

FIGS. 6A-B compare a square Euclidean electrode with a fractal interconnect, according to an embodiment of the present invention.

FIGS. 7A-C illustrate a one-dimensional line, a two-dimensional square, and a fractal structure with dimension between 1 and 2, such as used in a fractal interconnect according to an embodiment of the present invention.

FIGS. 9A-B are diagrams comparing two similar fractal structures having different fractal dimensions.

DETAILED DESCRIPTION

Figure 1A:
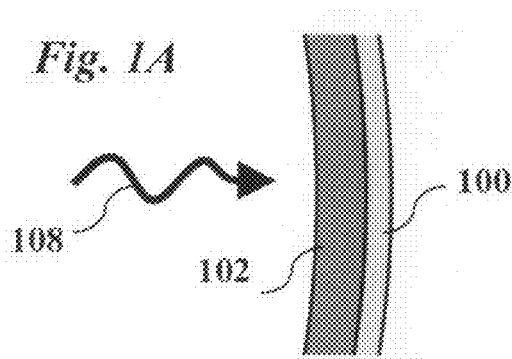
FIGS. 1A-C are schematic representations of the retina, a retina with an epiretinal implant, and a retina with a subretinal implant, respectively.
Figure 1B:
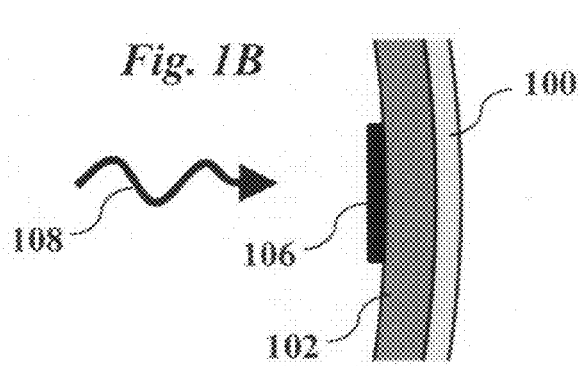
Figure 1C:
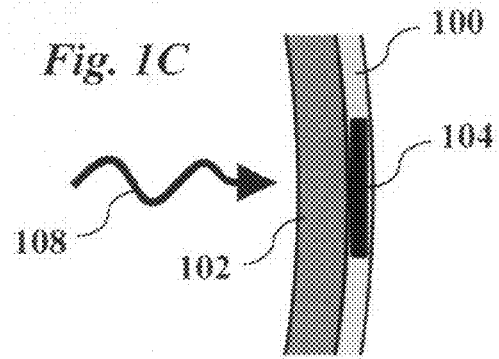

Embodiments of the present invention include a method for fabricating fractal interconnects to improve the neuro-electronic interface between biological organisms and artificial electronic implants such as artificial retinal implants, artificial brain implants and artificially-generated neuron systems. Embodiments also include neuro-electronic interconnect devices and the implant devices incorporating them. Such fractal interconnect devices provide a neuro-electronic interface between the electrodes of an implant and the neurons of a human or animal. The principles of the present invention have general application to many types of electronic implants and other devices that rely upon neuro-electrical interfaces.

FIG. 3A is a schematic diagram showing one embodiment of the invention in the form of an implant having an array of fractal interconnects 300 integrated with an electronic chip 302. For example, this type of device may be a retinal implant in the form of a 3 mm subretinal implant chip with an array of 5000 interconnects 300 that provide an improved neuro-electronic interface between electrodes of the implant and the neurons in the eye's plexiform layer.

FIG. 3B is a schematic diagram showing another embodiment of the invention in the form of a device in which an array of fractal interconnects 304 connects neuronal circuitry via wiring 306 to an external (non-implanted) device 308 that measures electrical signals originating in the connected neurons or stimulates the neurons to produce desired neuronal activity. In the case where the interconnects 304 are implanted, the neurons would be within the human or animal. This device, however, may also be used in cases where the interconnects 304 are not implanted in vivo but used to measure or stimulate neurons in vitro.

FIG. 3C is a schematic diagram showing another embodiment of the invention in the form of an implant having two arrays of fractal interconnects 310 and 312 joined by a cable 314 and possibly additional circuitry (not shown). Such an implant may be used to connect separate neuronal structures in an organism, e.g., between different parts of the brain or between severed parts of a peripheral nerve or between neurons in a Petri dish.

The fractal interconnects may not only be beneficial for establishing electrical contact between retinal implants and the dendritic structure of retinal neurons but also to the other neural networks of the body, such as neurons in the brain and even to artificially grown neurons. In addition, implants using this interconnect can be used to reestablish connection between two regions of neurons in the retina or the brain, which have been disconnected by damage to neurons.

As is evident from the above discussion, the fractal interconnects have applications to various types of devices that rely upon neuro-electronic interfaces. Many of the basic principles and features of the fractal interconnects are common to these applications. Accordingly, without loss of generality, for the purposes of definiteness much of the following description will focus on the fabrication and use of fractal neuro-electric interconnects in the context of subretinal implants.

The following discussion of the principles of fractal interconnects according to the present invention will help provide an appreciation of their unique features and advantages. First, we begin with the following definitions that will be used in the context of this application:

"Nanoscale"—having one or more dimensions in the range 0.5 to 1000 nm.

"Atomic Cluster" or "Cluster"—a nanoscale aggregate of atoms, typically comprising between 2 and $10^7$ atoms, having a size less than 100 nm.

"Nanoparticle"—a nanoscale particle, which includes atomic clusters.

"Substrate"—an insulating or semiconducting layer of material providing structural foundation for the fabrication of a device.

"Conductive"—electrical conductivity greater than $10^5$ S/m.

"Non-conductive"—electrical conductivity less than $10^{-5}$ S/m.

"Electrode"—an electrical conductor used to connect an object to an electrical circuit or electrical device.

"Interconnect"—an electrical conductor used to connect an object to an electrode.

"Euclidean"—of or relating to a geometry that is characterized by an integer dimension.

"Scaling plot"—a graph of log(NV) plotted against $log(L_0/L)$, where N is the number of boxes occupied by an edge of the pattern, L is the length of the box, and $L_0$ is the object's width, according to the principles of the standard box-counting analysis.

"Coarse limit"—the largest length L at which the box-counting analysis can distinguish between the analyzed pattern and a two-dimensional object of width $L_0$.

"Fine limit"—the smallest length L at which the box-counting analysis can distinguish between the analyzed pattern and a one-dimensional line.

"Scaling range"—the magnification range between the coarse and fine limits.

"Scaling gradient"—the slope of the tangent to the curve of the scaling plot at a specific scale L.

"Fractal"—a pattern that obeys the power law relationship $N(L) \approx L^{-D}$, where D is the fractal dimension, within a scaling range of at least one order of magnitude of magnification, according to the principles of the box-counting analysis.

"Fractal dimension"—the exponent of the power law relationship $N(L) \approx L^{-D}$, according to the principles of the box-counting analysis. The fractal dimension has a fractional value between 1 and 2. The fractal dimension is the average of the scaling gradients over the scaling range. These gradients vary by less than 10%.

"Dendrite"—an object with branching structure at multiple length scales, where values of the scaling gradients are between 1.1 and 1.9 over the scaling range.

"Fractal dendrite"—a dendrite having fractal dimension between 1 and 2.

"Fractal interconnect"—an interconnect with a fractal dendritic structure.

"Island"—an isolated aggregate of atomic clusters deposited on a substrate.

"Connectivity"—the percentage of electrodes or interconnects successfully connected to retinal neurons.

"Node"—a region where an electrode or interconnect overlaps with, and establishes electrical connection to, a neuron.

"Cross-links"—the number of nodes that connect interconnects to one neuron.

"Areal overlap"—the summation of the areas of all the nodes that connect to one neuron.

"Transmission area"—the percentage of the area of the photodiode that is not blocked by the fractal interconnect or electrode.

"Implant"—an electrical implant in a human or animal body.

"Diffusion-limited aggregation"—the process by which structures are generated from the aggregation of particles undergoing random Brownian motion.

"Edge diffusion"—the diffusion of particles along the border of an object.

"Coalescence"—the process by which two or more nanoparticles join and merge to become one structure.

"UHV"—ultra high vacuum, typically ~$10^{-9}$ Torr.

"Charge density"—charge-per-phase divided by the electrochemically active electrode surface area, where charge-per-phase is defined as the integral of the stimulus current over one half-cycle of the stimulus duration.

"Inert gas aggregation"—a technique for synthesis of nanoscale clusters of tunable size.

"Atomic cluster evaporation"—a technique for synthesis of nanoscale clusters by evaporation of atomic clusters from a crucible, where there is a natural preference for evaporation of clusters instead of atoms.

Figure 2A:
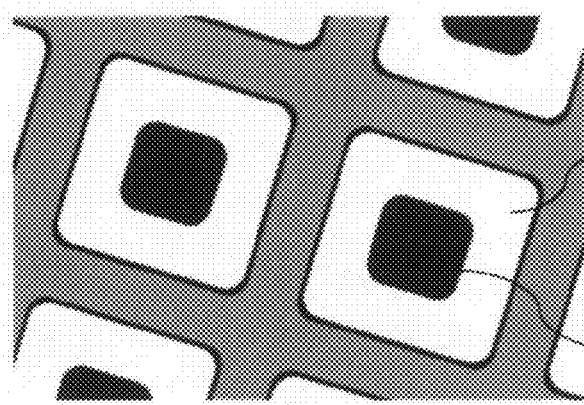
FIG. 2A is a detail view of the surface of a conventional subretinal implant showing two photodiodes having electrodes positioned in their centers.
Figure 2B:
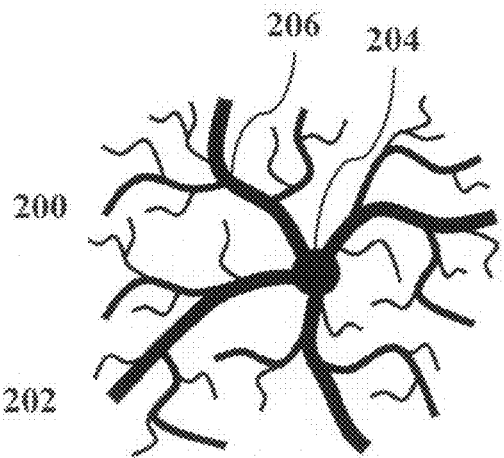
FIG. 2B is a schematic cross-sectional diagram of a retinal neuron.
Figure 4A:
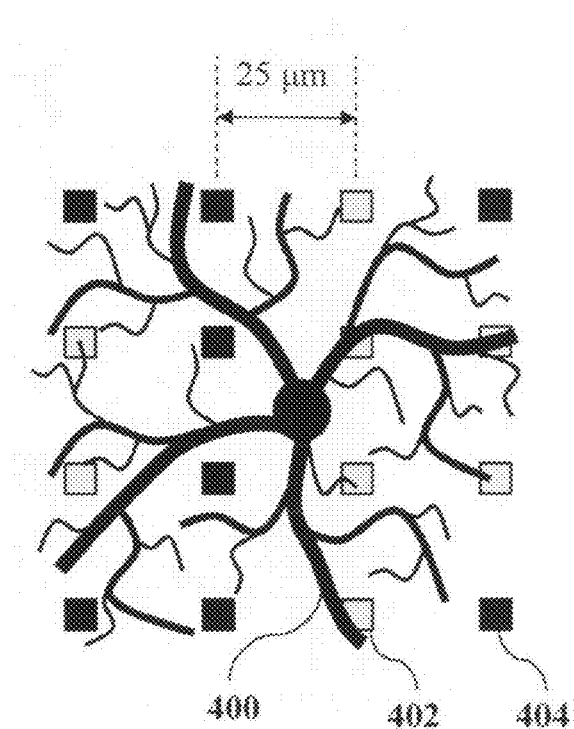
FIG. 4A is a schematic of an array of Euclidean electrodes overlaid on a retinal neuron.
Figure 4B:
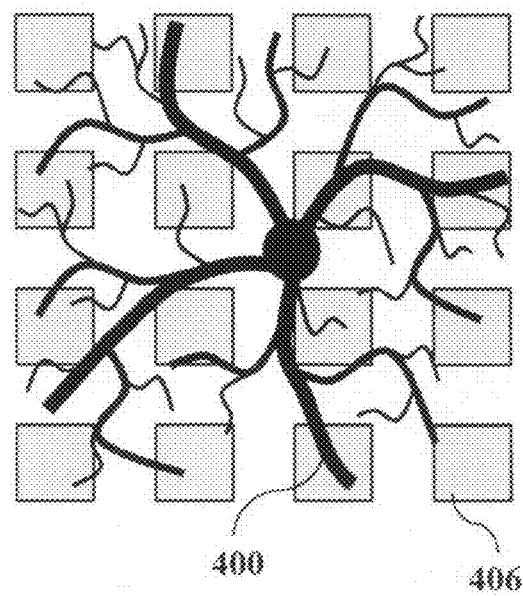
FIG. 4B is a schematic of an array of Euclidean electrodes overlaid on a retinal neuron.

To better appreciate the advantages of the fractal interconnects of the present invention, consider again the conventional array of electrodes 202 shown in FIG. 2A. Each of these electrodes has a square cross-section and has a Euclidean dimension of two. To illustrate the connectivity problems of this design, FIG. 4A shows an array of such Euclidean electrodes superimposed on a neuron 400. The neuron is 80×100 μm in size and each electrode is 10 μm wide. For clarity, the photodiodes are not shown. As is evident from the figure, half of the electrodes (shaded grey), are in contact with the neuron, e.g., electrode 402. However, the other half of the electrodes (shaded black), do not contact the neuron, e.g., electrode 404. Consequently, because half of the electrodes make no neuro-electrical connection with the neuron (i.e., a connectivity of only 50%), the signals from their corresponding photodiodes are not communicated to the neurons. It should be emphasized that increasing the surface roughness of the electrodes 404 does not help address this connectivity problem. FIG. 4B illustrates an array whose electrodes have larger Euclidean area (20 μm wide), thereby increasing the number of connections between the electrodes and the neuron. Increasing the electrode area, however, is not desirable for retinal implants since the larger electrodes will block even more light from reaching the photodiodes. In other words, although electrodes such as electrode 406 now connect with the neuron, their increased size prevents much of the incoming light from reaching the underlying photodiodes.

Figure 4C:
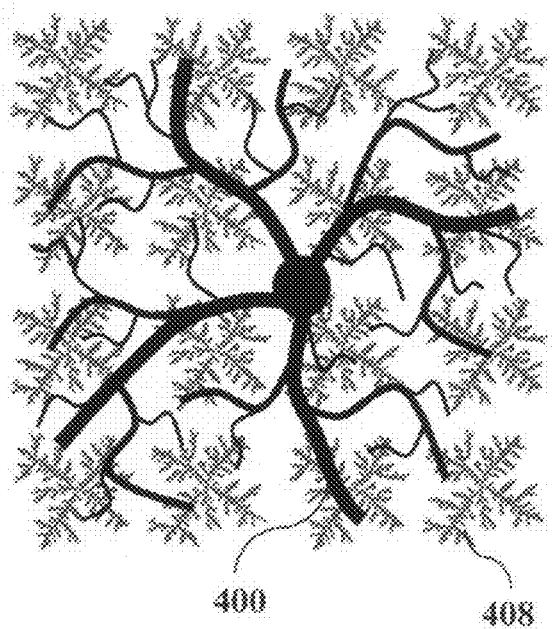
FIG. 4C is a schematic of an array of fractal interconnects overlaid on a retinal neuron, according to an embodiment of the invention.

Fractal interconnects according to the principles of the present invention overcome the above problems with interconnects formed from an array of Euclidean electrodes. As shown in FIG. 4C, an array of fractal interconnects, e.g., interconnect 408, are used instead of an array of Euclidean electrodes. Specifically, rather than interconnects with Euclidean dimension two (or fractal dimension greater than two, due to surface roughness), the fractal interconnects of the present invention are dendrites with a fractal dimension less than two. As a result, the connectivity provided by the fractal interconnects is dramatically superior to that of the array of Euclidean electrodes. For example, the connectivity of FIG. 4C is 100% compared to 50% for FIG. 4A. At the same time that it provides significantly larger connectivity, the fractal interconnect still allows light to pass through it and reach the underlying photodiode. Moreover, because the fractal interconnects spread out from each of the electrodes to span a 20 μm width, smaller electrodes may be used, thereby increasing light transmission to the photodiodes. The electrodes at the center of each interconnect 408 are not shown due to their significantly reduced size. Furthermore, due to their extended span, fractal interconnects also ensure that the high connectivity is insensitive to the relative positioning of the neuron and the array of interconnects.

Figures 5A, 5B:
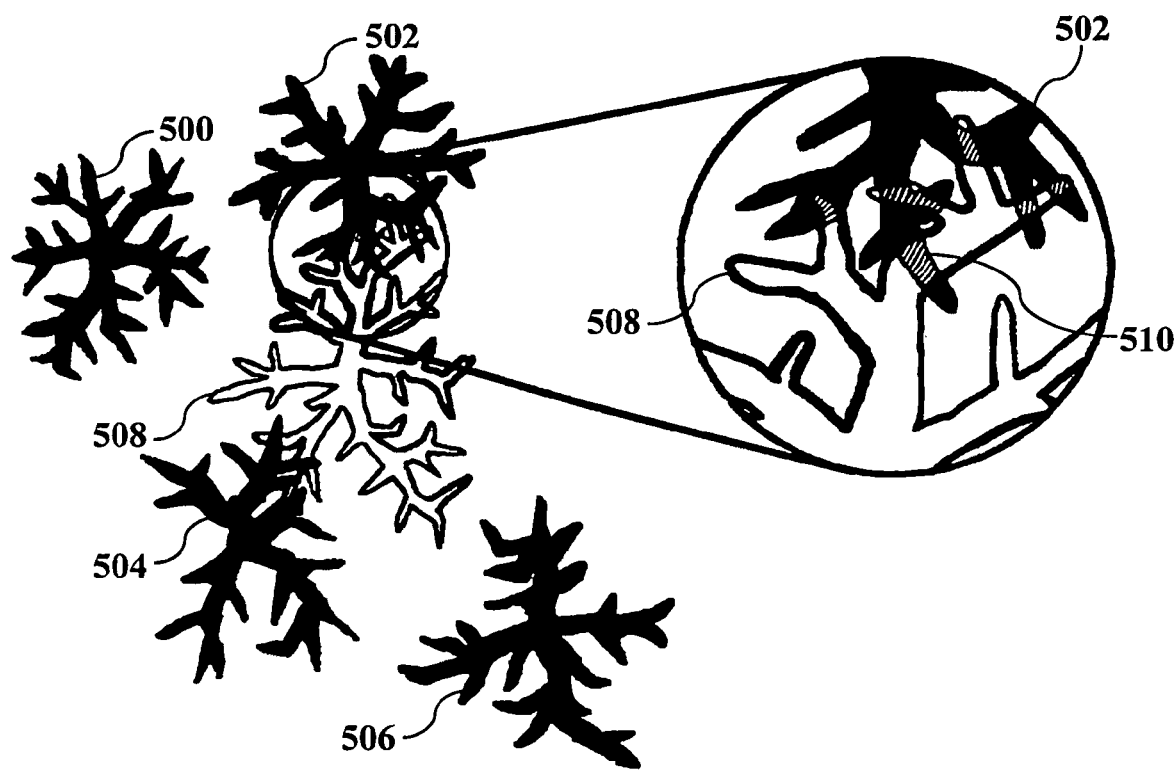
FIGS. 5A-B schematically illustrate the connectivity, cross-linking, and areal overlap of two fractal structures, according to the principles of the present invention.

In addition to increased connectivity, the fractal interconnects also provide increased cross-linking and areal overlap, as will now be described. The electrical connection established between one neuron and an array of interconnects (or, in the case of contemporary implants, an array of electrodes) may be quantified by three parameters, as demonstrated by FIGS. 5A-B. The schematic representation of FIG. 5A shows four fractal interconnects 500, 502, 504, 506 (black) and a neuron 508 (white). The connectivity is defined as the percentage of the number of interconnects that are in contact with at least one neuron, which in this example is 50%. A node or cross-link is defined as a region where an electrode or interconnect overlaps with (and establishes electrical connection to) a neuron, as represented by the crosshatched regions in FIG. 5B, such as node 510. The total areal overlap of a neuron is the combined area of the nodes of the neuron. These three connection parameters provide a measure of the connection of the interconnects to an individual neuron. We note that FIGS. 5A-B is a simplified representation for sake of illustration. In reality, the dendrites belonging to a number of neurons will partially overlap each other. Returning again to FIG. 4C, it is apparent that the number of cross-links provided by the fractal interconnects is significantly larger than the number of cross-links in FIG. 4A. The large number of nodes may increase both the redundancy and reliability of the neuro-electronic connections, which can be especially valuable in cases where the neurons are damaged or may degenerate. Moreover, since each node can deliver a signal bias to the neuron, the increase in number of nodes may cause an increase in signal, allowing smaller voltages to be used. Lower voltages can reduce the likelihood of voltage-induced damage and also limit the generation of toxins due to polarization of electrolytic bio-fluids at the interface.

In addition to the increased connectivity and cross-linking, the use of fractal interconnects can also significantly increase the areal overlap compared to the Euclidean electrodes. This increased areal overlap may reduce the charge density at the neuro-electronic interface, which is expected to decrease the probability of voltage-induced damage to the retinal circuitry.

In the case of retinal implants, the fractal interconnect also has the important advantage that the connectivity to neurons is increased while at the same time allowing transmission of light to the photodiodes of the retinal implant. This becomes clearer by comparing a conventional Euclidean square electrode 600 shown in FIG. 6A to the fractal interconnect 604 shown in FIG. 6B. Whereas the Euclidean electrode 600 blocks 25% of the area of the underlying photodiode 602, the interconnect 604 and significantly smaller electrode 606 block significantly less of the area, allowing more light to reach the underlying photodiode 608. At the same time, the fractal interconnect 604 branches out and provides better connectivity with neurons. Thus, the fractal interconnect is more adept at spanning space without blocking large areas.

It should be noted that the wavelength of the longest form of visible light is approximately 800 nm. Thus, to ensure direct transmission of light through the gaps between the branches of the fractal to the underlying photodiode, the scale of the microarray and fractal interconnects for a retinal implant are preferably sufficiently large that the gaps between the dendritic branches are larger than this wavelength. However, for gaps smaller than 800 nm, plasmon physics suggests that the fractal pattern may in certain circumstances act as a 'super lens' to aid transmission of the light to the photodiodes. These specific effects may depend on various factors such as the regularity of the fractal pattern, the scaling range of its fractal properties, and its fractal dimension.

To better understand some of the specific advantageous properties of the fractal interconnects, it is helpful to understand various properties of fractals, specifically as they apply to a fractal dendrite, which is a specific form of a dendritic object in which the branches repeat at increasingly small length scales. To further quantify the favorable properties of the interconnects, we consider the fractal characteristics of the fractal dendrite in more detail. The branching structure of the fractal dendrite—large branches split into smaller branches, which in turn split into smaller branches, and so on—can be characterized by the fractal dimension, D.

For Euclidean shapes, the fractal dimension D is equal to its Euclidean dimension—for a point D=0, for a straight line D=1 (FIG. 7A), and for a flat area D=2 (FIG. 7C). However, the fractal dimension D of a fractal shape is not equal to its Euclidean dimension. For example, the D value of a dendritic tree that spreads out in a plane (FIG. 7B) lies between one and two, representing the fact that, although it locally (i.e., at very high magnification) resembles lines with Euclidean dimension one, its overall pattern (i.e., at zero magnification) extends over an area with Euclidean dimension two. By increasing the amount of branching at increasingly fine size-scales, the shape fills more area, and the D value moves closer to two.

Figure 8A:
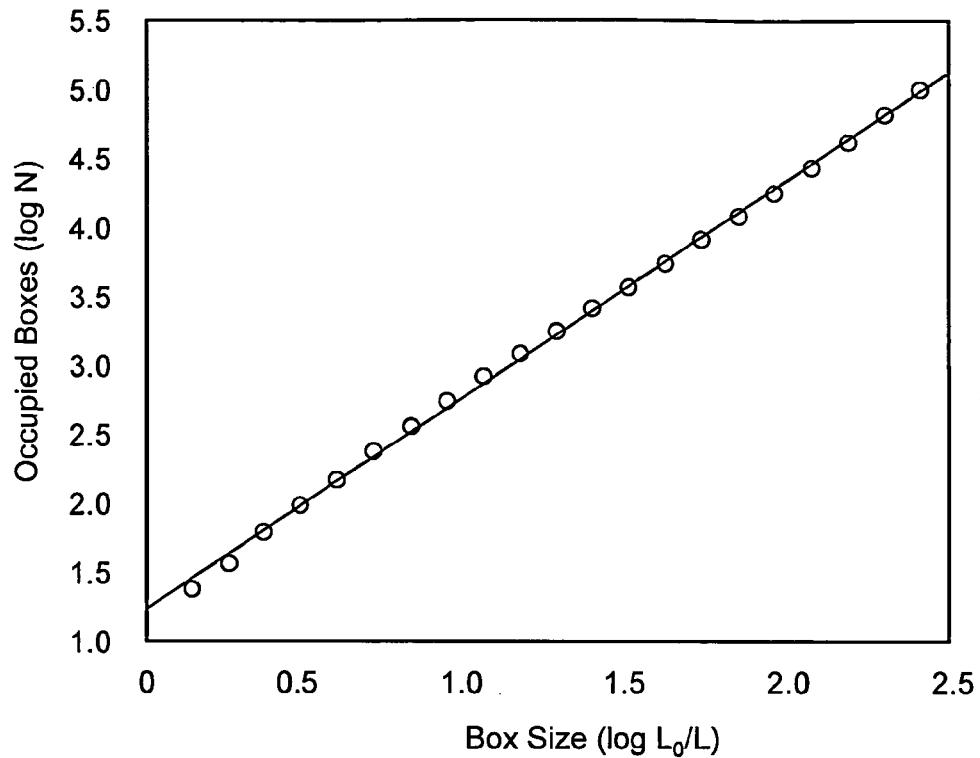
FIG. 8A is a scaling plot derived from a box counting analysis of an image of a neuron projected onto a plane, showing that the neuron image has a fractal dimension of 1.7 over a scaling range of more than two orders of magnitude.

The fractal dimension may be determined using the well-established "box-counting" analysis on an image of a fractal object. Using this technique, a mesh of identical squares ("boxes") of size L are superimposed on the image. The number of squares, N(L), that contain any part of the object is then counted. This is repeated for different sizes, L, of the squares in the mesh. The count N(L) gives a measure of the space coverage of the pattern at magnification L, and reducing the square size is equivalent to looking at this coverage at larger magnifications. For fractal behavior, N(L) satisfies the power law relationship $N(L) \approx L^{-D}$, where D has a constant non-integer value over the scaling range, which spans between the coarse and fine limits. For fractal behavior, this scaling range must be greater than one order of magnitude in magnification. This power law is illustrated by a straight line in the scaling plot of $\log(N(L))$ versus $\log(L_0/L)$, where $L_0$ is the width of the object, and the D value is the slope of the line. For example, the box-counting method applied to an image of a retinal neuron projected onto a plane produces the scaling plot shown in FIG. 8A which has a straight line with constant slope D=1.7 over more than 2 orders of magnitude of magnification (the coarse and fine limits occur at $\log(L_0/L)$ values of 0.5 and 2.5 respectively).

Figure 8B:
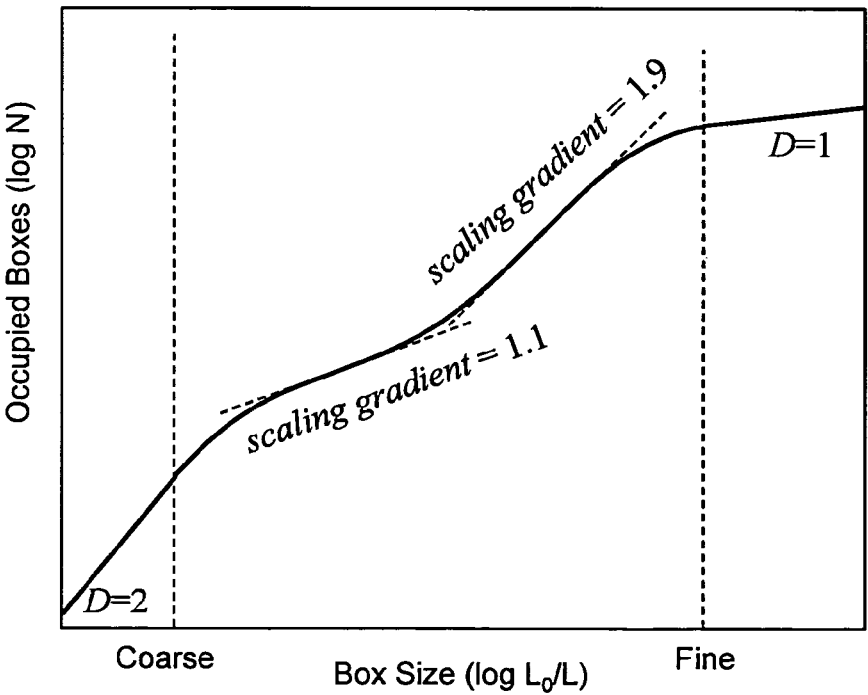
FIG. 8B is a scaling plot of a dendrite, showing scaling gradients that vary between 1.1 and 1.9 over a scaling range of more than one order of magnitude of magnification between a fine limit and a coarse limit.

Some dendrites may not have a constant D value over the scaling range, but nonetheless still have branching properties at multiple scales. FIG. 8B, for example, is a scaling plot of a non-fractal dendrite, showing scaling gradients that vary between 1.1 and 1.9 over a scaling range of more than one order of magnitude of magnification. If the scaling gradient is constant with a non-integer value, or has only a small variation, over at least a decade of magnification, then the dendrite may be called a fractal. More generally, a fractal may be defined as an object whose scaling gradient is a non-integer value and varies by less than 10% (or, more preferably, by less than 5%) over at least one order of magnitude of magnification, and the average value of its scaling gradient over such a range of magnification may be defined as its fractal dimension.

In view of the above, the fractal interconnects of the present invention are understood to include dendritic structures that have a well-defined fractal dimension (i.e., whose scaling gradients vary by less than 10%). Also, it is understood that, while the present description focuses on embodiments having fractal interconnects, the interconnects of the invention also include non-fractal dendritic interconnects whose scaling gradients are more variable, e.g., structures whose scaling gradients within a scaling range are contained between 1.1 and 1.9.

The fractal branching of a neuron is typically characterized by a D value that can vary from 1.68 for a cat's retinal neuron to 1.7 for a human's retinal neuron. FIGS. 9A-B illustrate similar fractal structures with different values of D. In FIG. 9A the structure has fractal dimension that is lower compared to the fractal dimension of the structure shown in FIG. 9B. It is evident that the structure in FIG. 9B with the larger fractal dimension spans the space just as effectively while having less Euclidean area, i.e., allowing more light to be transmitted through the structure.

The fractal dimension is correlated with various favorable functional characteristics of fractal objects. In particular, characteristics such as large perimeter lengths of the fractal object and the associated increase in connectivity arise from the repetition of spatial structure across several decades of magnification. These characteristics can be enhanced by adjusting two crucial factors. The first factor is the power law exponent D, which describes how the patterns occurring at different magnifications branch to build the resulting fractal shape. Since D corresponds to the gradient of the scaling data, it charts the 'rate' at which structure is added through progressive magnification: a high fractional D value corresponds to a higher rate of branching, which leads to a higher ratio of fine to coarse structure in the pattern. The second factor is the magnification range over which this fractal scaling occurs, i.e., the magnification scale cut-offs between which the fractal dimension D remains constant. A mathematical fractal can have an infinite scaling range because the fractal repetition can occur between infinitely large and infinitely small size scales. In contrast, a physical object has a finite scaling range somewhere between a large size-scale limit (set by the size of the object) and a small size-scale limit (set by the smallest distinguishable features of the object).

Dendritic interconnects with any branched geometry will provide advantages in functionality of the interconnects compared to Euclidean electrodes. However, the greatest advantages will be enjoyed by fractal dendrites which will provide greater connectivity, more interconnects, and more areal overlap than simple branching structures without any fractal characteristics. Because the advantages are expected in most cases to increase for fractal branches characterized by high D fractals and large fractal scaling ranges, in many embodiments it is preferable that D is greater than 1.4 and less than 1.9. In some applications, it is preferred that fractal interconnects are characterized by a D value of 1.6-1.9, or more preferably 1.7, so that they that they approximately match the D value of neurons.

In most cases, functionality will also be improved by larger fractal scaling ranges. A fractal scaling range of at least 1.0 order of magnitude of magnification is preferred for the beneficial fractal properties to manifest themselves. More preferably, the fractal scaling range should extend at least 2.0 orders of magnitude, and more preferably at least 2.5 orders of magnitude. For example, in a specific embodiment of a fractal interconnect array in a retinal implant, the interconnects have more than one order of magnitude of fractal scaling range below 200 µm, and more preferably at least two orders of magnitude of fractal scaling range below 200 µm. In another embodiment, they have at least 2.6 orders of magnitude of fractal scaling range, extending from large scale branches spanning 20 µm down to the finest scale of 50 nm.

To summarize, as is evident from the discussion above, there are several advantages that the fractal interconnects may provide in many embodiments:

- The fractal interconnects establish a higher connectivity to a neuron compared to the Euclidean electrodes.
- The high connectivity of the fractal interconnects is robust to alignment errors between the relative positions of the implant and the neurons.
- The fractal interconnects minimize and may eliminate any need to attach neurons to the implant before implantation surgery.
- Increased areal overlap between a neuron and the fractal interconnects reduces the charge density at the interface, which reduces both electrical damage to the neuron and voltage-induced toxins.
- The fractal interconnect provides an increased number of nodes between the electrode and the neuron. This provides a redundancy in connection to safeguard against failed connections. It also establishes a multi-channel electrical circuit analogous to the neural circuits in the retina and the brain. The interconnects can therefore be used to reestablish connection between neurons by replacing damaged neurons in the retina and the brain.
- The fractal interconnects provide an excellent balance of the three electrical connection parameters (connectivity, cross-linking, and areal overlap) between the interconnects and the neuron and maximal transmission of light through the interconnects. This balance is important for the operation of subretinal implants.

Figure 10:
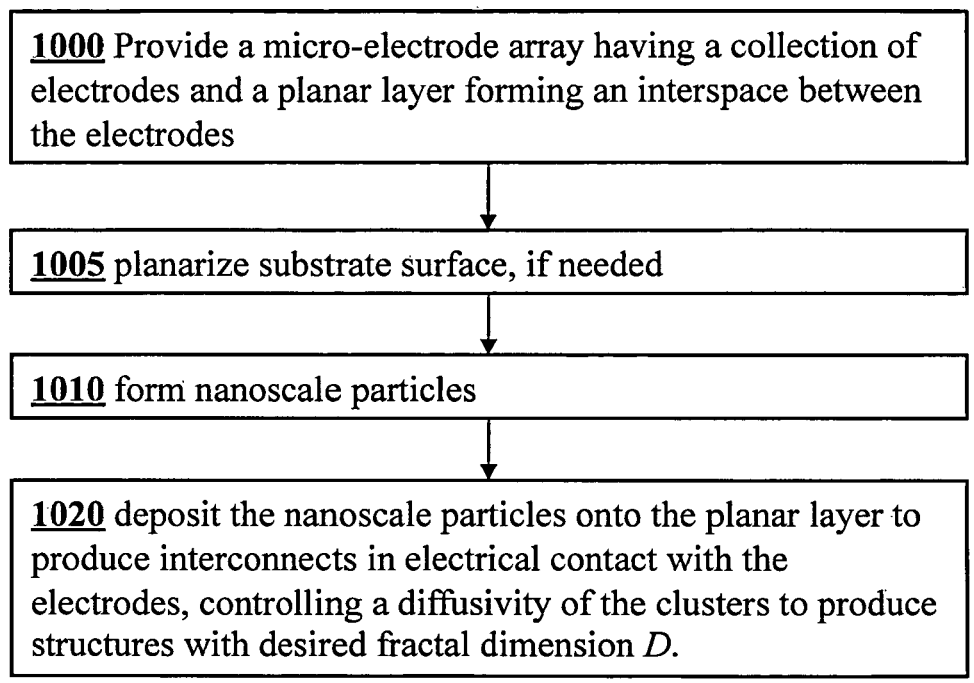
FIG. 10 is a flow chart outlining the steps of a method for fabricating fractal interconnects according to an embodiment of the invention.

The details of the structure and fabrication of a device according to preferred embodiments of the invention will now be described. In a preferred embodiment, a method of fabricating fractal interconnects for a retinal implant is outlined in FIG. 10. The method includes, in step 1000, providing a micro-electrode array having a collection of electrodes and a semiconductor or insulating planar layer forming a non-conductive interspace between the electrodes. In some embodiments, e.g., for retinal implant devices, the micro-electrode array may take the form of a photodiode array with each electrode connecting to a corresponding photodiode. The fabrication of the photodiode array is preferably performed using conventional techniques such as standard optical lithography. In one embodiment, a 3 mm wide chip is fabricated with 5000 photodiodes and electrodes in an array. In other embodiments, the array may have one or more electrodes, numbering from 1 to 50,000 or more, on a semiconductor chip 1-10 mm in diameter or larger. In some embodiments, the micro-electrode array may be an array fabricated as part of a microelectronic implant device, and the methods of the present invention serve to augment such a device by fabricating on its surface an array fractal interconnects.

In some embodiments, if the surface roughness inhibits diffusion-limited aggregation of the nanoparticles, the method may also include planarizing the surface of the array in step 1005. A smooth surface is desired to promote proper growth of the fractal interconnects. The substrate surface on which the clusters are deposited is preferably smooth, i.e., the surface has a mean roughness (Rms) less than 1 nm. Most preferably, the surface is atomically flat. The smooth surface does, however, have the electrodes protruding and thereby serving as nucleation sites for the formation of the fractal interconnect. FIGS. 11A-F illustrate various planarization techniques. The cross-sectional side views shown in FIGS. 11A-D detail four elements of an array. The top views shown in FIGS. 11E-F detail the appearance of a single array element in FIGS. 11A-B.

Figure 11A:
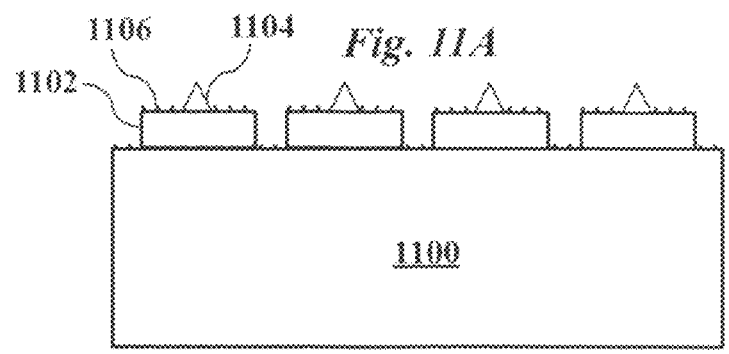
FIG. 11A is a cross-sectional schematic of a retinal implant device prior to deposition of fractal interconnects, according to an embodiment of the present invention.
Figure 11E:
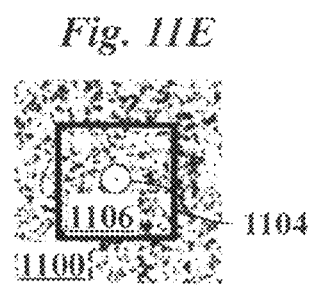
FIGS. 11E-F are top views of the surfaces of the devices shown in FIGS. 11A-B, respectively, according to an embodiment of the invention.
Figure 11B:
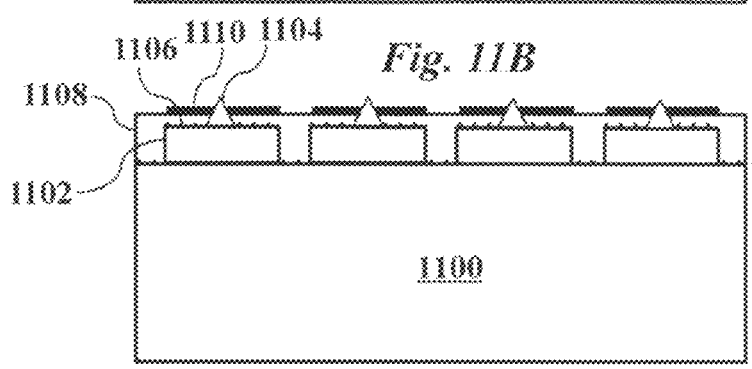
FIG. 11B is a cross-sectional schematic of a retinal implant device after fractal interconnects are grown on a planarized surface deposited above the photodiodes, according to an embodiment of the invention.
Figure 11F:
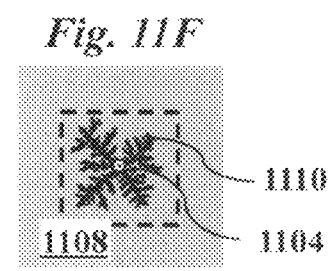

FIG. 11A shows a substrate 1100 with photodiodes 1102 fabricated on its surface. On the surface 1106 of each photodiode 1102 is fabricated an electrode 1104. FIG. 11E shows the corresponding photodiode from the top. In the case where surface 1106 is rough, the clusters may lock in place where they land on the device. Consequently, such a rough surface is unsuitable for the creation of fractal interconnects. Accordingly, FIG. 11B shows the same array having a supplementary smooth platform 1108 fabricated on top of the substrate and photodiodes so that the clusters can properly diffuse. Platform 1108 is fabricated so that the tips of the electrodes 1104 protrude through its surface and thereby serve as nucleation sites for the fractal interconnects 1110. FIG. 11F shows the corresponding top view. The platform 1108 is an electrical insulator or semiconductor. For example, the platform may be created using standard deposition techniques and may be composed of silicon nitride, $MoS_2$, mica, SU-8 or other photoresist, or spin-coating (poly)methyl methacrylate (PMMA). For retinal implants, the platform 1108 is preferably transparent to optical wavelengths. In a preferred embodiment, the electrodes 1104 are fabricated smaller than in conventional implants to avoid unnecessarily blocking light from reaching the photodiode 1102.

Figure 11C:
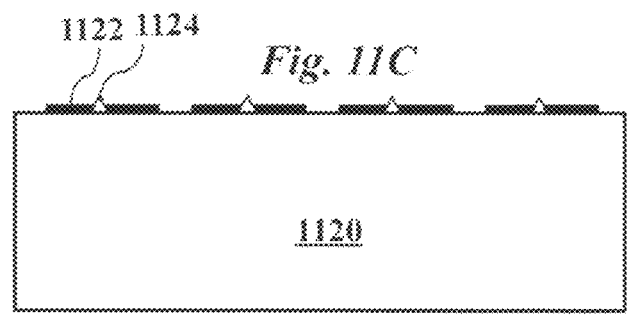
FIG. 11C is a cross-sectional schematic of a generic implant having fractal interconnects grown directly on the substrate, according to an embodiment of the invention.
Figure 11D:
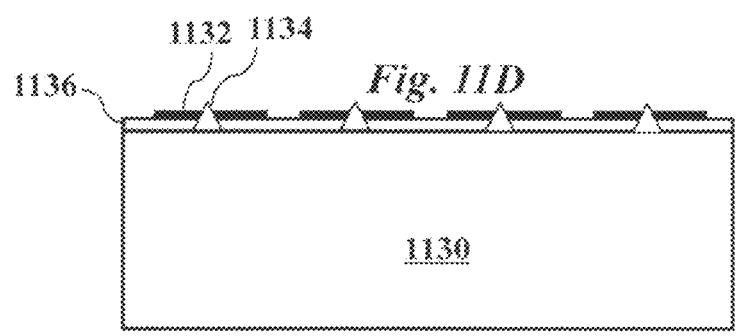
FIG. 11D is a cross-sectional schematic of a generic implant device in which fractal interconnects are grown on a planarized surface deposited on the substrate, according to an embodiment of the invention.

FIG. 11C shows the design of an implant that does not incorporate photodiodes. In this device, the substrate 1120 has a surface that is already sufficiently smooth to allow diffusion of clusters during the growth of fractal interconnects 1122 centered around the small electrodes 1124. An additional planarization layer is thus not needed in this case. FIG. 11D shows another design of an implant without photodiodes. This device has a rougher substrate surface 1130 that is unsuitable for the formation of fractal interconnects. Accordingly, a planarization layer 1136 is deposited as in FIG. 11B to provide a smooth surface upon which the fractal interconnects 1132 are grown around electrodes 1134. The corresponding top views are similar to FIG. 11F.

Returning now to FIG. 10, in step 1010 nanoscale particles are formed by a technique such as inert gas aggregation (IGA) or atomic cluster evaporation (from a crucible). In IGA, a metal vapor (e.g., Ag, Pt, Pd, Au, Sb, or Bi) is evaporated via crucible heating or by sputtering into a flowing inert gas stream (e.g., Ar or He) that causes the condensation of the metal vapor into particles that can range from a few atoms to about 100 nm in size. The particles are carried through a nozzle by the inert gas stream so that a molecular beam is formed. Particles transported by the beam can then be deposited onto a suitable surface.

Ionized clusters and/or a mass selection system may be used in a deposition system, for example incorporating a mass filter, as described by B. von Issendorf et al. in *Rev. Sci. Inst.* 70, 4497 (1999), and cluster ionization by a standard electron beam technique. A feature of a preferred deposition system, as described by R. Reichel et al. in *J. Nanopart. Res* 8, 405 (2006), which is not typically incorporated into most vacuum deposition systems, is the use of electrical feed-throughs into the deposition chamber to allow electrical measurements to be performed on devices during deposition. Such feed-throughs are standard items supplied by most companies dealing in vacuum equipment.

In a typical example, antimony clusters are produced in an inert-gas aggregation source. In the source chamber, bulk antimony is heated up and evaporated at temperatures ranging from 980-1160° C. Helium gas at room temperature mixes with the metal vapor and the clusters nucleate and start to grow. The cluster/gas mixture passes two stages of differential pumping (from ~1 Torr in the source chamber down to less than ~$10^{-6}$ Torr in the deposition chamber) such that most of the gas is extracted. At the sample, the diameter of the cluster beam is about 10 mm. In order to determine the intensity of the cluster beam, a quartz crystal deposition rate monitor is used. The samples are mounted on a movable rod and are positioned in front of the quartz deposition rate monitor during deposition. Similarly, silver clusters can be produced by evaporating bulk silver at temperatures ranging from 850-1030° C. and clusters formed in the same manner.

Note that the specific range of source parameters appears not to be critical: clusters can be produced over a wide range of pressures (0.01 Torr to 100 Torr) and evaporation temperatures and deposited at almost any pressure from 1 Torr to $10^{-12}$ Torr. Any inert gas, or mixture of inert gases, can be used to cause aggregation, and any material that can be evaporated may be used to form clusters. The cluster size is determined by the interplay of gas pressure, gas type, metal type, metal evaporation temperature and nozzle sizes used to connected the different chambers of decreasing pressure.

Returning to FIG. 10, in step 1020 the nanoscale particles are deposited onto the planar layer to produce fractal interconnects in electrical contact with the electrodes. The diffusivity of the clusters is controlled during the deposition such that each of the produced interconnects has a fractal dimension D between 1.4 and 1.9 over a scaling range of at least one order of magnitude below 200 μm.

Figure 12A:
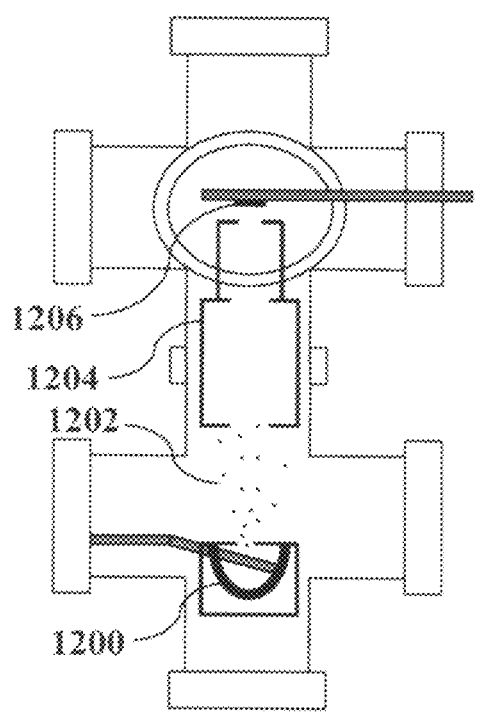
FIG. 12A is a schematic representation of a UHV apparatus used to fabricate Sb islands, according to an embodiment of the invention.

According to one implementation, the method involves diffusion-limited aggregation. In a preferred embodiment, deposition of either atomic vapor or very small clusters can be achieved by evaporation from a simple crucible arrangement in an ultra high vacuum chamber, such as shown in FIG. 12A. High purity metals (Ag, Sb, Bi) are evaporated from a crucible 1200. Thermal evaporation of antimony is known to produce a vapor comprised exclusively of $Sb_4$ particles as described by J. Mühlbach et al., in *Surf Sci.* 106, 18 (1981); similarly, evaporation of Bi leads to production of predominantly $Bi_2$ particles.

Figure 12B:
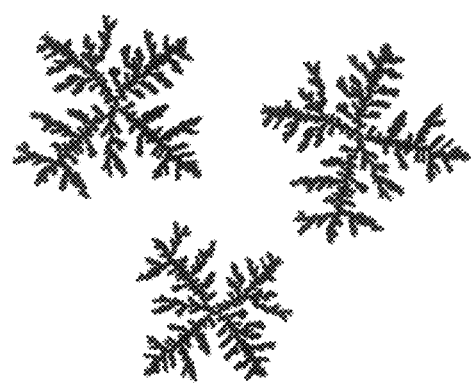
FIG. 12B illustrates fractal interconnect islands grown on a substrate in the apparatus of FIG. 12A, according to an embodiment of the invention.

The clusters in the form of vapor 1202 are transported through baffles 1204 and deposited on the substrate 1206 at temperature, T, with particle flux, F, and coverage, θ, monitored with a calibrated quartz crystal microbalance. The initial clusters diffuse along the surface until encountering an electrode where they nucleate. After nucleation, subsequent clusters aggregate at the site driven by the dynamics of diffusion-limited aggregation (DLA) to form fractal structures, as shown in FIG. 12B. The characteristics of the fractal structure that results are determined by edge diffusion and coalescence. The four main variables controlling the outcome are flux, coverage, substrate temperature, and cluster size. FIG. 12B shows islands of antimony ($Sb_4$) clusters deposited on HOPG (highly-oriented pyrolitic graphite).

Increasing the particle flux reduces the available time for transport of particles along the perimeter of the island before the next particles arrive from the diffusion field and 'pin' the previous material in place. The appropriate flux range is typically 0.001-10.0 Å/s. In a preferred embodiment the flux is in the range 0.1-10.0 Å/s.

The coverage is measured in units of monolayers (ML) where 1 ML is defined as the average inter-atomic distance in the bulk metal of choice, e.g. 3.1 Å for antimony. The useful coverage can range between approximately 0.01 ML and 100 ML. In a preferred embodiment the coverage is in the range 1-10 ML.

Temperature control of the substrate surface can be used to change the diffusivity of clusters, for example to allow clusters to diffuse on surfaces on which they would otherwise be immobile, or to increase edge diffusion. Lowering the temperature of the substrate lowers the diffusivity, which inhibits islands from reducing their surface energy, by reducing edge diffusion. This leads to islands exhibiting a more highly branched shape. The range of temperatures that can be used is limited by the melting point of the clusters. The diffusivity also relies on the cluster size. Larger clusters diffuse slower, thereby increasing the complexity of the island's shape.

The chamber is typically vented with dry nitrogen one hour after deposition.

Figure 13A:
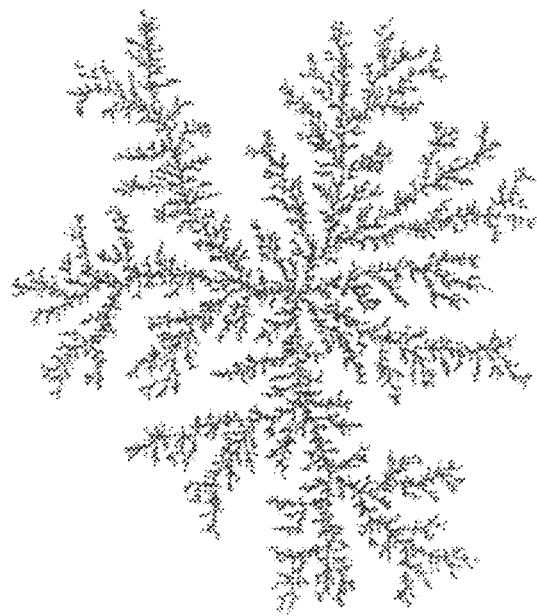
FIGS. 13A-C illustrate similar fractal structures having different fractal scaling ranges, according to embodiments of the present invention.
Figure 13B:
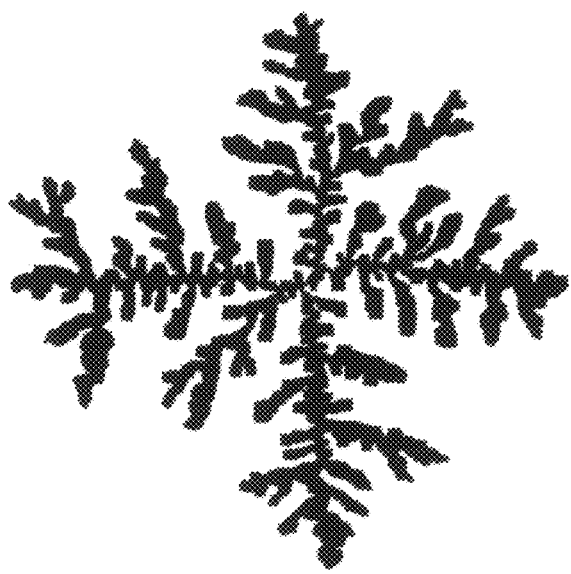
Figure 13C:
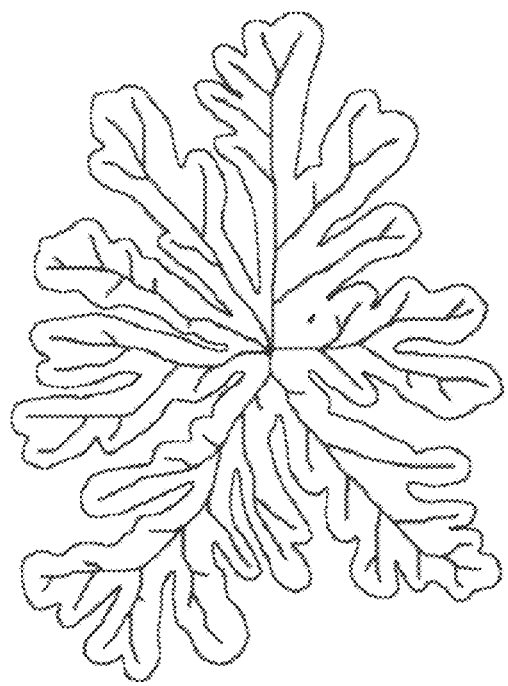
Figure 14:
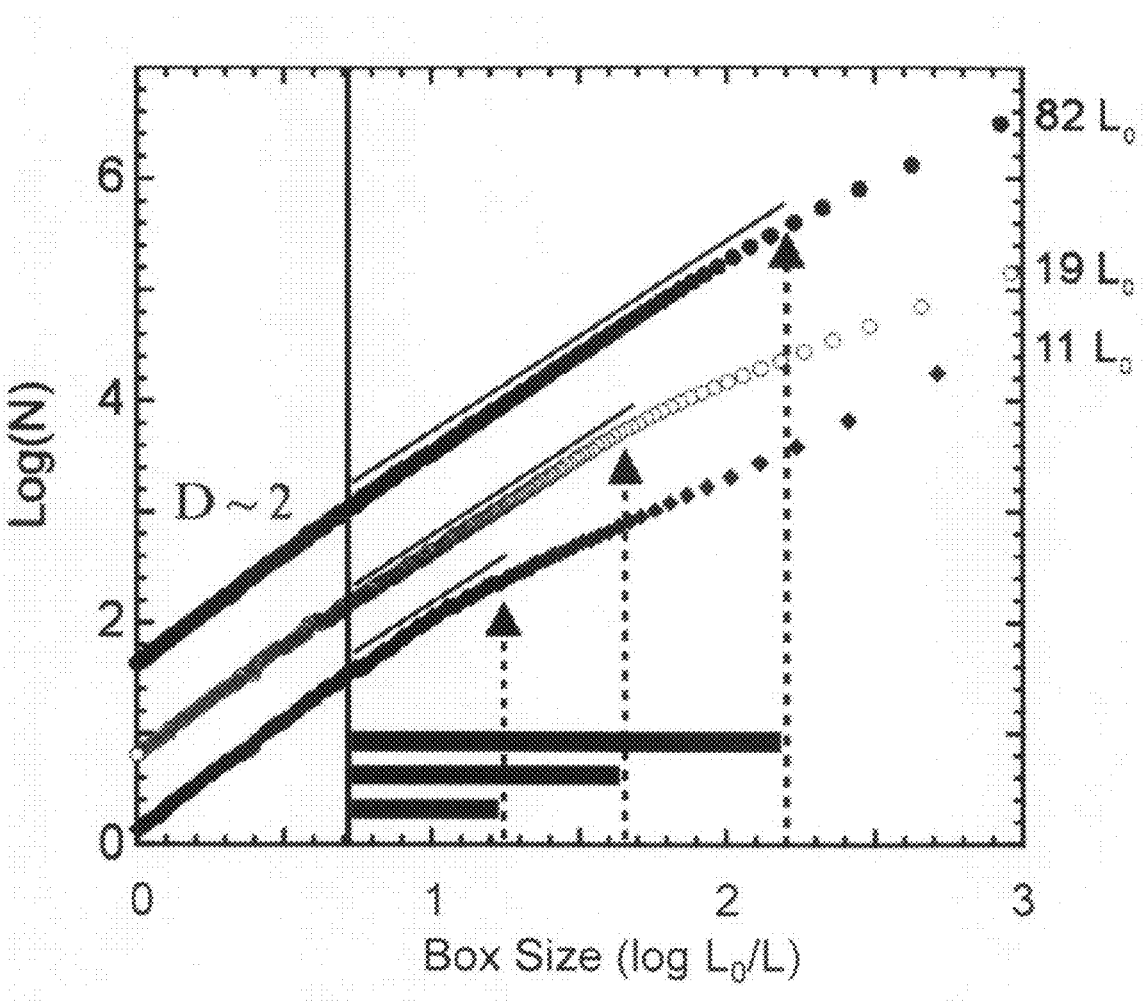
FIG. 14 is a scaling plot resulting from a box-counting analysis applied to FIGS. 13A-C.

The scaling range of a physical fractal object can only occur between the coarse limit (determined by the size of the object) and the fine limit (determined by the basic building blocks of the object). This can be demonstrated by considering the three fractal structures shown in FIGS. 13A-C which have been subjected to the above mentioned box-counting analysis, the results of which are shown in FIG. 14. The bars and arrows in FIG. 14 indicate the extent of each island's fractal scaling range. In those scaling ranges, black lines indicate the D=1.7 gradient. Outside the fractal scaling range, D≈2 at large box sizes where all boxes contain part of the island, and D≈1 at box sizes smaller than the finest features of the island. The dotted and dashed lines indicate D=2 and D=1, respectively. The perimeter of each pattern is also indicated at the fine scale end of the plot. These three fractals have the same fractal dimension, and they each have the same coarse limit set by their identical diameters. However, the three fractals have different fine limits: the fractal scaling of the object in FIG. 13A persists to much finer scales than that of FIG. 13B, which in turn persists to smaller scales than the object of FIG. 13C. Consequently, the three fractals have different fractal scaling ranges. We will now discuss in more detail how the different growth conditions determine the fine limit of fractal scaling.

As an example of the variable growth processes and their effects on the fractal parameters, we will compare islands grown from very small atomic clusters and two models of this growth process. First, consider the formation of simulated fractal patterns, which are based on classical diffusion-limited aggregation (DLA) of atomic clusters. In DLA simulations, particles are released from a boundary on the substrate and diffuse freely until they encounter a stationary particle fixed to the surface. Once this encounter has occurred, the particle has its position fixed and the process is repeated. FIG. 13A shows a simulated dendritic pattern generated from approximately 100,000 particles. This DLA island displays the fractal patterning created by the repetition of structure across many size scales.

However, for DLA islands formed from atomic clusters, this simple model is inadequate to describe the physics governing the growth process. The physical growth conditions can strongly affect the branching structure of the islands. By increasing the deposition rate, island size, cluster size, or decreasing the substrate temperature, the islands feature fractal structure to increasingly fine size scales. The associated increase of the fractal scaling region improves the island's connectivity and thus its effectiveness for interfacing elements such as electrodes and neurons. The fractal scaling range can also be increased by generating fractal structures to larger size scales. This is achieved by growing larger islands (as measured by the island's width $L_0$). Depositing more material results in larger, more highly branched structures with correspondingly larger fractal scaling ranges.

Taking into account the above considerations, a more physically realistic simulation can be developed to model the DLA process based on a model described by J. Zhong et al. in *Phys. Rev. B* 63 113403 (2001). Specifically, in such a DLA model multiple particles are allowed to impinge anywhere on the substrate (as if from a beam of atomic clusters) rather than single particles released from a boundary. The model allows tuning the relative rates of particle deposition, particle diffusion along the edges and corners of the island, and island reordering (coalescence). Each of these describes a process that occurs during the deposition of atomic clusters on a substrate and their presence has the effect of smoothing out the finest branches. FIG. 13B illustrates a result of such simulation. It closely resembles the physical pattern created by deposition of $Sb_4$ clusters on HOPG substrates, as shown in FIG. 13C. To facilitate a visual comparison of the simulated islands with the grown $Sb_4$ islands, FIG. 13C shows the boundary edge of one of the $Sb_4$ islands traced as well as a 'backbone' pattern to highlight the coarse scale branching structure. Whereas the coarse scale structure of the grown $Sb_4$ island is visually reminiscent of the DLA simulation, the island's edge clearly lacks the first simulation's fine structure (FIG. 13A). This absence of fine structure in the grown $Sb_4$ dendrite is due to an increased prevalence of the particle diffusion effects.

The scaling plots of FIG. 14 show how the differing growth conditions of the islands of FIGS. 13A-C impact their D values and their scaling ranges. The D value for the simulated island of FIG. 13A matches the well-established value for DLA of 1.7. This scaling 'rate' is preserved for all three plots in FIG. 14, which indicate that the changing growth conditions have not modified the basic particle dynamics of the fractal generation process: all three islands are formed from a DLA process. However, the changing growth conditions have reduced the magnification range over which the DLA operates, as illustrated by the horizontal bars at the base of the scaling plot. This corresponds to a gradual suppression of fine scale branching by edge diffusion and cluster coalescence. To emphasize the importance of this reduction of magnification range on functional properties, we compare the perimeter lengths of different islands. The pure DLA island of FIG. 13A has a perimeter of 82 $L_0$, reduced to only 11 $L_0$ in FIG. 13C, where $L_0 \approx 2.2$ µm. In contrast, a perfect (mathematical) fractal would have an infinite boundary due to its ever increasing fine scale features. Because a reduction in fine structure branches would decrease the connectivity between two fractal dendrites, which is an important factor for our fractal interconnect design, it is preferred that the fine structure branches be large, corresponding to a larger scaling range.

In light of the teachings and principles described above, fractal interconnects can be grown with various desired properties including fractal dimension and scaling range, thereby providing specific advantageous features for improved neuro-electronic interconnects. In addition to DLA techniques described above, other methods may be used to fabricate the interconnects of the invention, e.g., photolithography.

After fabrication, the device may be encapsulated in a biocompatible coating, one embodiment being encapsulated in a soft silicone body as typical of standard techniques for preparing implants.

An important characteristic of the fractal interconnects formed by the method of the invention is that in general they will provide enhanced connectivity to biological fractal structures such as neurons, which in turn give rise to a number of applications. Applications of the devices include:

Interconnecting the electrodes of subretinal and epiretinal implants to the neural structures of the eye;

Interconnecting electrodes of implants to the optic nerve;

Interconnecting different regions of the retina to reestablish deteriorated connections;

Interconnecting external electrodes to the brain (currently used, for example, to provide deep brain stimulation to regions of the brain damaged by Parkinson's disease);

Interconnecting regions of the brain to reestablish deteriorated connections (in pathological conditions such as Alzheimer's and Parkinson's disease, which damage highly localized regions, leaving surrounding neurons unaffected);

Interconnecting the electrodes of prosthetic limbs to the nerves of the body;

Interconnecting different parts of the nervous system to reestablish deteriorated connections;

Interconnecting electrodes to neurons for the purpose of probing or experimental testing of the response of the neurons to external stimuli, such as drugs, light or psychological factors;

Interconnecting electrodes to artificially assembled networks of neurons (e.g. in Petri dishes); and Interconnecting two networks of artificially assembled neurons.

The invention claimed is:

1. A neuro-electronic interface device comprising:
a micro-electrode;
an interconnect in electrical contact with the micro-electrode;
wherein the interconnect is conductive and is fabricated on a non-conductive surface;
wherein the interconnect is a dendrite having scaling gradients that vary between 1.1 and 1.9 over a scaling range of more than one order of magnitude of magnification.

2. The device of claim 1 wherein the interconnect has a fractal dimension D equal to a value between 1.4 and 1.9 over a scaling range of at least one order of magnitude below 200 µm.

3. The device of claim 1 further comprising:
an array of micro-electrodes; and
an array of interconnects in electrical contact with the array of micro-electrodes;
wherein the interconnects are in one-to-one correspondence with the micro-electrodes.

4. The device of claim 1:
wherein the non-conductive surface is a non-conductive planar layer fabricated on a substrate;
wherein the micro-electrode is fabricated on the substrate;
wherein a surface roughness of the planar layer is less than a surface roughness of the substrate.

5. The device of claim 4 wherein the planar layer has a mean roughness (Rms) less than 1 nm.

6. The device of claim 5 wherein the planar layer is atomically flat.

7. The device of claim 1 wherein the interconnect has a fractal dimension between 1.6 and 1.9 over a scaling range of at least two orders of magnitude below 200 µm.

* * * * *